United States Patent
Sullivan et al.

(10) Patent No.: US 11,603,759 B2
(45) Date of Patent: Mar. 14, 2023

(54) METHOD AND SYSTEM FOR DETERMINING ASPHALTENE ONSET PRESSURE

(71) Applicant: SCHLUMBERGER TECHNOLOGY CORPORATION, Sugar Land, TX (US)

(72) Inventors: Matthew T. Sullivan, Westwood, MA (US); Christopher Harrison, Auburndale, MA (US); Elizabeth Jennings Smythe, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 281 days.

(21) Appl. No.: 16/651,969

(22) PCT Filed: Sep. 26, 2018

(86) PCT No.: PCT/US2018/052871
§ 371 (c)(1),
(2) Date: Mar. 27, 2020

(87) PCT Pub. No.: WO2019/067552
PCT Pub. Date: Apr. 4, 2019

(65) Prior Publication Data
US 2020/0256189 A1 Aug. 13, 2020

Related U.S. Application Data

(60) Provisional application No. 62/564,390, filed on Sep. 28, 2017.

(51) Int. Cl.
*E21B 49/08* (2006.01)
*E21B 47/06* (2012.01)
(Continued)

(52) U.S. Cl.
CPC .......... *E21B 49/0875* (2020.05); *E21B 47/06* (2013.01); *E21B 49/088* (2013.01);
(Continued)

(58) Field of Classification Search
CPC .... E21B 49/0875; E21B 49/087; E21B 47/06; E21B 49/088; E21B 49/10; G01N 21/3577; G01N 33/2823; G01N 2015/0092
See application file for complete search history.

(56) References Cited

U.S. PATENT DOCUMENTS

| 8,910,514 B2 | 12/2014 | Schlumberger |
| 2002/0139929 A1 | 10/2002 | Mullins et al. |

(Continued)

OTHER PUBLICATIONS

H. Dumont, et al., "Asphaltene and Saturation Pressure Detection with DFA While Pulling out of Hole on Wireline", SPWLA-2016-II.
(Continued)

*Primary Examiner* — Caroline N Butcher
(74) *Attorney, Agent, or Firm* — Frederick Carbone

(57) ABSTRACT

Asphaltene onset pressure of a formation fluid is determined by subjecting the fluid to a plurality of tests where depressurization is conducted at a different depressurization rate for each test while optically monitoring the fluid for asphaltene flocculation. The pressures at which asphaltene flocculation are detected in each test are fit to a curve as a function of depressurization rate, and the curve is extrapolated to a pressure (e.g., 0 psi) to provide the asphaltene onset pressure.

23 Claims, 12 Drawing Sheets

(51) Int. Cl.
*E21B 49/10* (2006.01)
*G01N 33/28* (2006.01)
*G01N 21/3577* (2014.01)
*G01N 15/00* (2006.01)

(52) U.S. Cl.
CPC ......... *E21B 49/10* (2013.01); *G01N 21/3577* (2013.01); *G01N 33/2823* (2013.01); *G01N 2015/0092* (2013.01)

(56) References Cited

U.S. PATENT DOCUMENTS

| | | |
|---|---|---|
| 2005/0134845 A1 | 6/2005 | Bordelon |
| 2010/0263442 A1 | 10/2010 | Hsu et al. |
| 2011/0093200 A1 | 4/2011 | Hsu et al. |
| 2014/0268156 A1 | 9/2014 | Schlumberger |
| 2015/0309002 A1* | 10/2015 | Fukagawa .............. G01N 21/59 356/70 |
| 2015/0309003 A1* | 10/2015 | Sullivan ............. G01N 21/3577 356/70 |
| 2017/0284197 A1* | 10/2017 | Dumont ................. E21B 47/07 |

OTHER PUBLICATIONS

International Preliminary Report on Patentability_dated Apr. 9, 2020 for international Patent Application PCT/US2018/052871 filed on Sep. 26, 2018.
International Search Report and Written Opinion_dated Dec. 3, 2018 for international Patent Application PCT/US2018/052871 filed on Sep. 26, 2018.

* cited by examiner

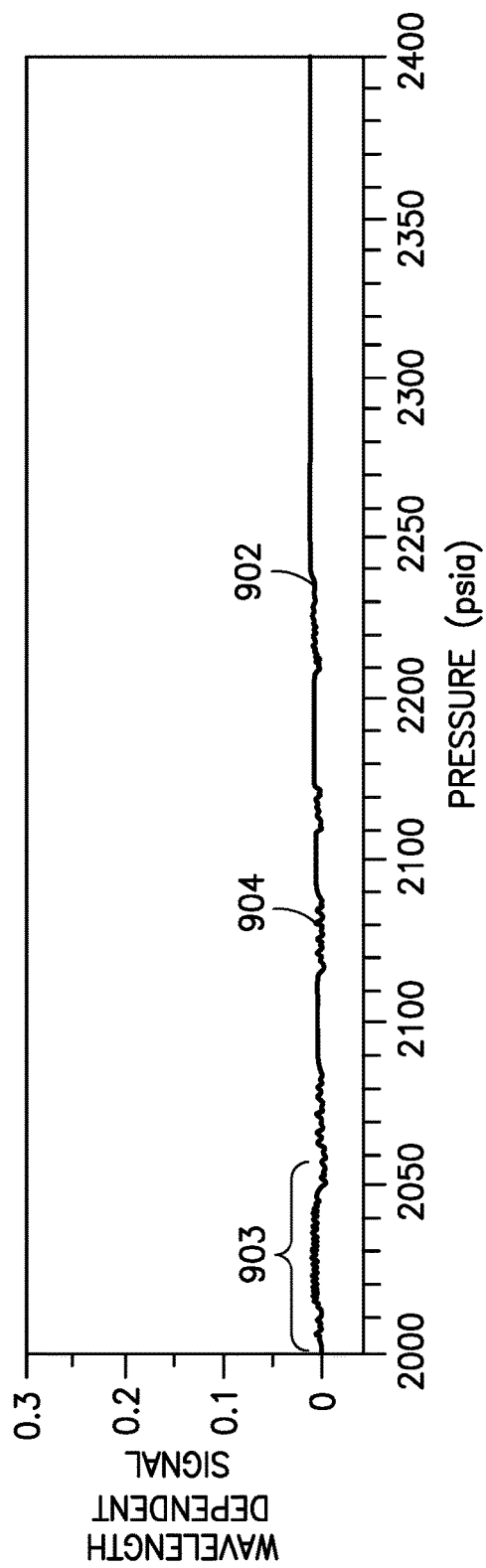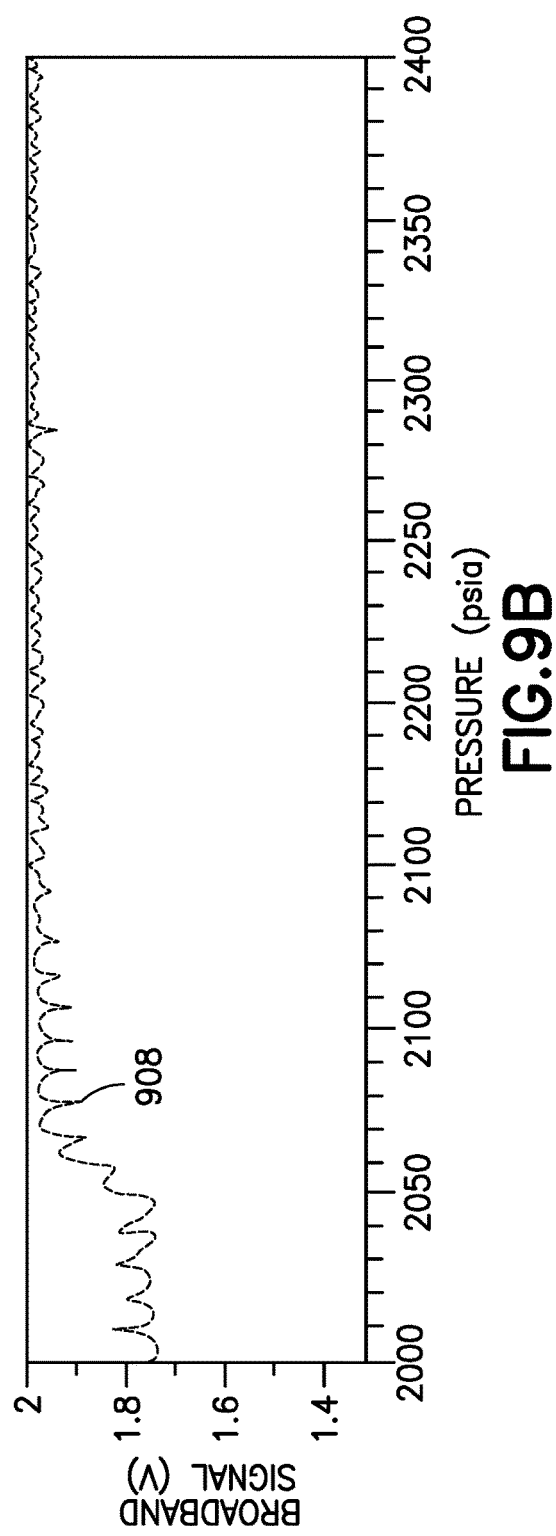

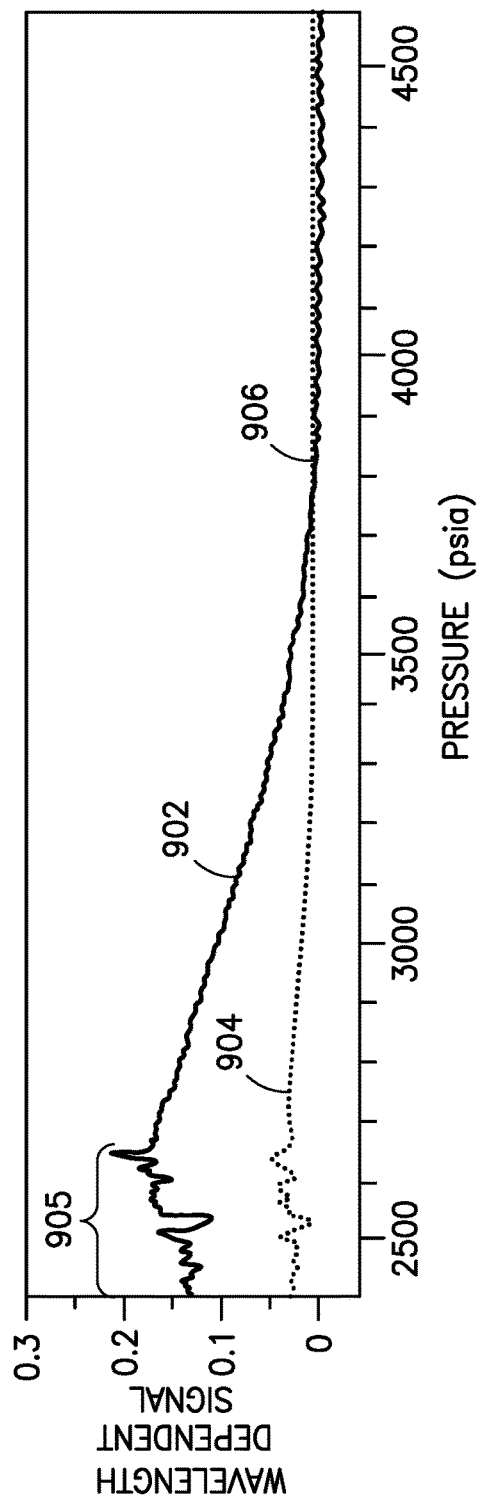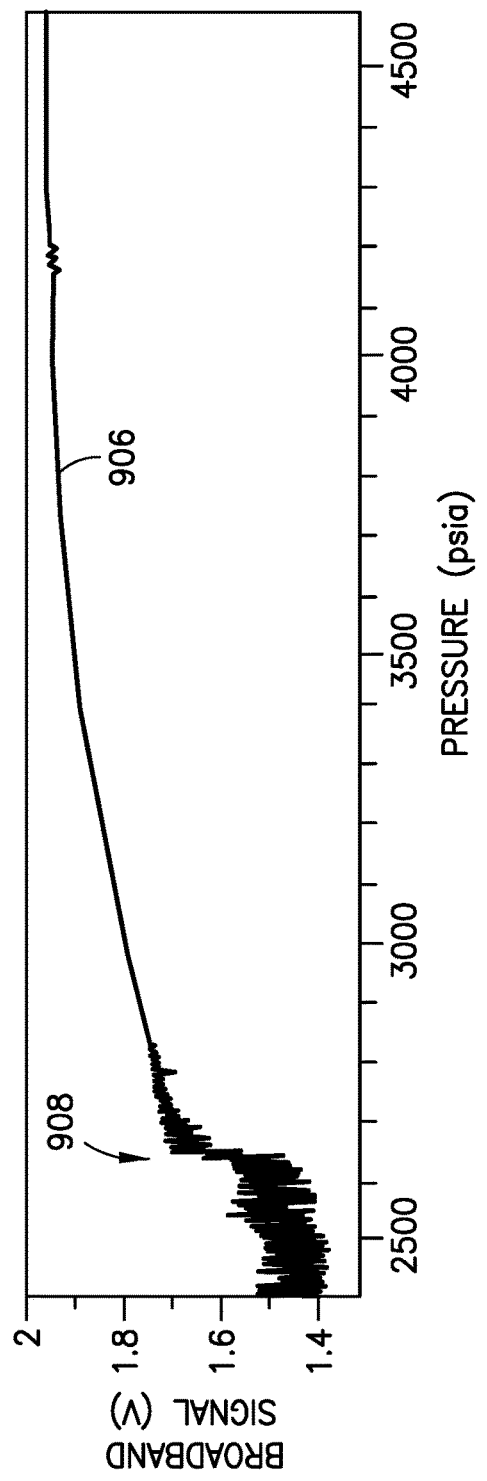

METHOD AND SYSTEM FOR DETERMINING ASPHALTENE ONSET PRESSURE

CROSS-REFERENCE TO RELATED APPLICATIONS

This application claims the benefit of priority under 35 U.S.C. 119(e) to U.S. Provisional Patent Application No. 62/564,390 filed Sep. 28, 2017, the entire contents of which are incorporated herein by reference.

FIELD

The present disclosure relates to fluid analysis, and more particularly to determining the asphaltene onset pressure of a fluid.

BACKGROUND

Asphaltenes are large polar molecules that are naturally dissolved in some oilfield formation fluids. At reservoir temperatures and pressures, asphaltenes are usually dissolved in the reservoir fluid. If the pressure of the fluid is decreased, as occurs during oil production, the solubility of the asphaltenes decreases: below a certain pressure the asphaltenes will begin to flocculate. The pressure at which this flocculation first occurs is known as the asphaltene onset pressure (AOP). Individual molecules join to form nanoaggregates, which then form clusters of nanoaggregates. The process of flocculation is illustrated in The subject disclosure is further described in the detailed description which follows, in reference to the noted plurality of drawings by way of non-limiting examples of the subject disclosure, in which like reference numerals represent similar parts throughout the several views of the drawings, and wherein:

FIG. 1.

For oil and gas companies, the AOP is a valuable piece of information needed to help characterize a well and determine appropriate production parameters. During the production of a well, the pressure in the reservoir and of the produced fluid is kept above the AOP to prevent flocculation from occurring. If the fluid pressure drops below the AOP, asphaltene accumulation can occur in the reservoir and production equipment. This accumulation can restrict flow, ultimately decreasing the output of the well and lowering its overall economic value.

Laboratory techniques to measure the AOP of a reservoir fluid directly measure the pressure at which asphaltene flocculation onset occurs. In one technique, light transmission through the sample is monitored as the sample pressure is lowered. The onset of asphaltene flocculates scatters the light illuminating the sample, causing a significant decrease in optical transmission: the highest pressure at which the transmission significantly decreases is the AOP. This measurement may be performed with a laser as the light source and the sample at reservoir temperature. Sample pressure is slowly lowered (~100 psi/hour) by increasing the isolated volume of the measurement fluid, while an impeller mixes the sample. This technique is illustrated in FIG. 2. A similar laboratory technique uses the same sample depressurization scheme, but determines the AOP by direct observation of flocculates instead of a decrease in optical transmission. For this measurement, a microscope is used to observe a portion of the sample volume during depressurization. While these two equilibrium techniques can be performed individually or simultaneously, neither is amenable to an in situ reservoir AOP measurement. The large volumes of sample, long time scale and mixing elements required for the measurements are prohibitive in a downhole environment.

Techniques to measure the AOP of a reservoir fluid downhole in an oil well are different than those used in a laboratory. One technique utilizes a wavelength dependent signal: a small volume of sample (less than 2 mm in depth) is illuminated by a broadband light source. Light transmitted through the sample is monitored on two or more detectors. Before reaching a detector, the light is directed through a bandpass filter, resulting in the detector signal being proportional to a specific wavelength range. Comparison of two or more of these filtered channels allows the asphaltene onset pressure of a fluid to be determined: as a sample is depressurized, the flocculation of asphaltenes will scatter more light at smaller wavelengths than at longer wavelengths. The pressure at which the change in two different wavelengths starts to diverge is taken to be representative of the AOP of the fluid while pulling out of hole. See H. Dumont, et al, "Asphaltene and Saturation Pressure Detection with DFA While Pulling out of Hole on Wireline", SPWLA-2016-II. However, it would be advantageous to perform such measurements while the downhole tool was still sampling at station, which the technique discussed here teaches.

An additional consideration when making an asphaltene onset pressure measurement is that the optical signal occurring at the AOP can be confused with the optical signal occurring at the bubble point pressure of the sample. The bubble point pressure is the pressure at which some of the gas dissolved in the reservoir sample is liberated, changing the sample from a single-phase liquid to a two-phase mixture of liquid and gas. As the pressure of the sample is decreased below the bubble point, the liberated gas forms bubbles. This process is illustrated in FIG. 3. These bubbles scatter light illuminating the sample, thereby decreasing the measured optical transmission. This change in optical transmission can be mistaken for the decrease caused by the flocculation of asphaltenes at the asphaltene onset pressure.

SUMMARY

The following summary is meant to help the understanding of one skilled in the art when reviewing the present disclosure and related claims. It is not meant in any way to limit the presented or future related patent claims.

Illustrative embodiments of the present disclosure are directed to a method for determining asphaltene onset pressure of a formation fluid. This method includes the following: (a) illuminating a sample of formation fluid with light; (b) starting at an initial starting pressure, depressurizing sample at a first depressurization rate; (c) detecting the intensity of light transmitted through the sample during depressurization; (d) determining a first flocculation pressure for the sample when a change in the optical signal due to asphaltene flocculation has occurred; (e) (re)pressurizing the same sample or another sample of the formation fluid to its initial starting pressure or to another pressure above the first flocculation pressure; (f) repeating (a) through (d) at least once using a second, different depressurization rate to obtain at least a second flocculation pressure for the sample (or another sample of the formation); (g) fitting a mathematical function to the first and second asphaltene flocculation pressures as a function of depressurization rate; (h) determining the asphaltene onset pressure of the formation fluid using the function. In one embodiment, the asphaltene onset pressure of the formation fluid is determined by using the function to calculate a flocculation pressure at an equivalent of a zero-depressurization rate.

Various embodiments of the present disclosure are also directed to a system for determining the asphaltene onset pressure of a formation fluid. This system includes both a source for generating the light transmitted through the sample of formation fluid and a detector for measuring light passing through the sample. The system further comprises apparatus for measuring and controlling the pressure of the sample, such that the rate of depressurization may be controllably varied. The system further includes a controller or processor that determines the asphaltene onset pressure of the formation fluid using the optical signals measured during at least two depressurizations.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein:

FIG. 9A is a plot of wavelength dependent signals as a function of fluid pressure during a depressurization of a sample with a bubble point and no asphaltene flocculation;

FIG. 9B is a plot of a broadband signal measured during the depressurization of a fluid sample with a bubble point but no asphaltene flocculation;

FIG. 9C is a plot of wavelength-dependent signals as a function of fluid pressure during a depressurization of a sample with a bubble point and asphaltene flocculation;

FIG. 9D is a plot of a broadband signal measured during the depressurization of a fluid sample with a bubble point and asphaltene flocculation;

DETAILED DESCRIPTION

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Illustrative embodiments of the disclosure are directed to a method and system for determining asphaltene onset pressure of a fluid sample, such as formation fluid. An illustrative method includes the following: (a) transmitting light through a sample of the fluid; (b) detecting intensity of light transmitted through the sample; (c) depressurizing the sample while continuing to transmit and detect light; (d) optionally, identifying if changes in the detected intensity of the light transmitted during depressurization is due to asphaltene flocculation; (e) identifying a pressure characterizing the change in optical intensity due to asphaltene flocculation; (f) increasing the pressure on the sample or on another similar sample and repeating (a)-(e) at least once at at least one different depressurization rate; and (g) determining an asphaltene onset pressure of the sample by interpolating the measured characteristic flocculation pressures at different depressurization rates to a depressurization rate of zero. In the illustrated embodiments, this method efficiently determines asphaltene onset pressure by utilizing measurements at two or more different depressurization rates, as opposed to a single depressurization rate. Details of the various embodiments are discussed below.

Figure 1:
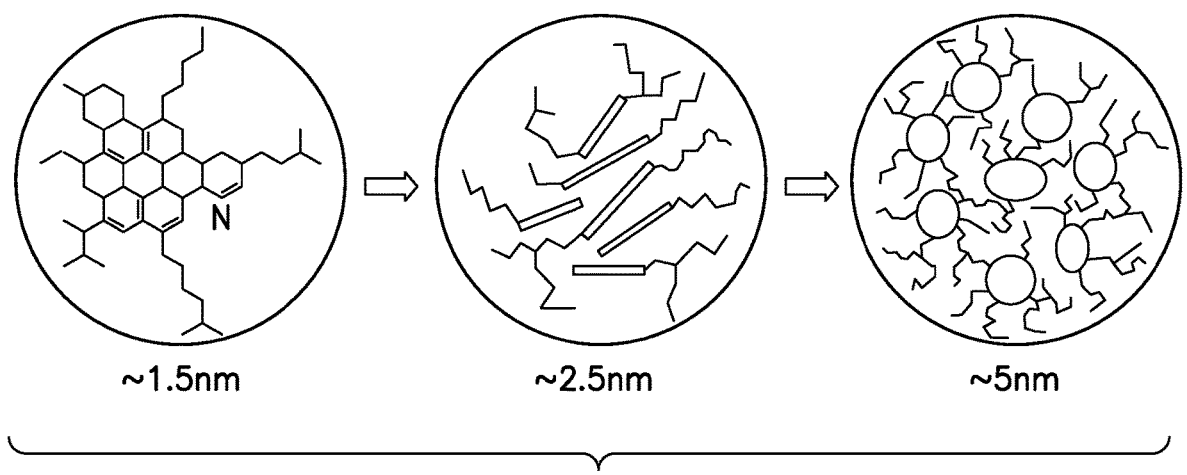
FIG. 1 illustrates the aggregation process of asphaltenes.
Figures 2, 3:
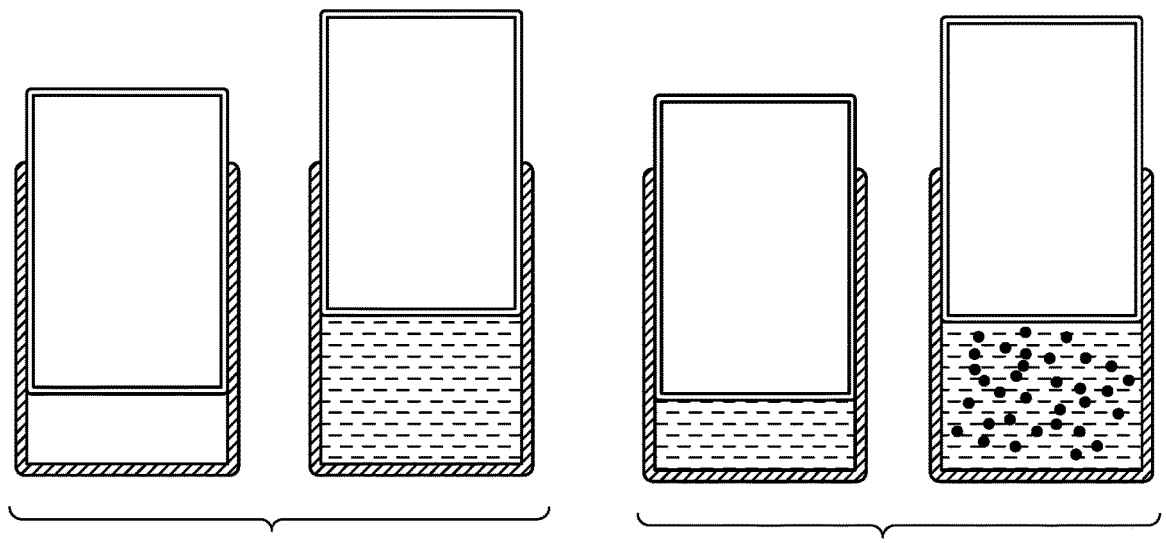
FIG. 2 shows an increase in sample opacity due to flocculation of asphaltenes within a formation fluid sample at pressures equal to or below the asphaltene onset pressure.
FIG. 3 illustrates the nucleation of bubbles in a sample of formation fluid at pressures equal to or below the bubble point pressure.
Figure 4:
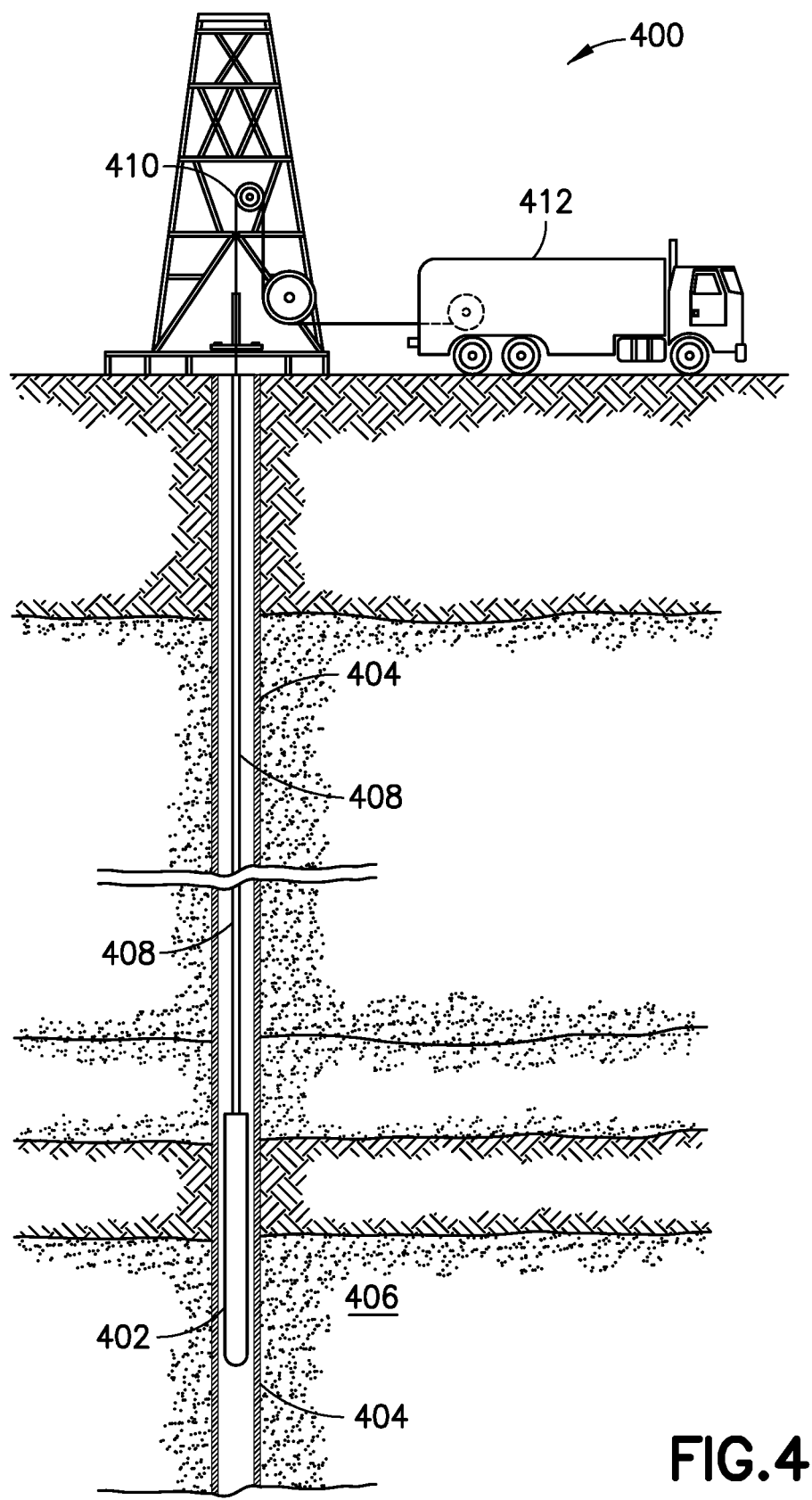
FIG. 4 is a schematic of a wireline logging system at a well site in accordance with one embodiment.

An example of a wireline logging system 400 at a well site is shown in FIG. 4. The measurements of asphaltene onset pressure described below can be implemented on this wireline logging system 400. In this example, a wireline tool 402 is attached to a cable 408. Using a winch 410, the tool 402 is lowered into a wellbore 404 which extends through (traverses) a reservoir formation 406 of interest. The wireline tool 402 is located in the reservoir 406 next to (adjacent) a location of interest and makes measurements of the reservoir fluid. The wireline tool 402 can be moved to make measurements at multiple locations of interest in the wellbore 404. A computer system located with the surface equipment 412 can be used for storing and processing the data acquired by the wireline tool 402. A cable 408 running between the wireline tool 402 and the surface equipment 412 can be used to transmit the acquired data and to communicate between the surface equipment 412 and the wireline tool 402. In this illustration, the surface equipment 412 includes a truck that supports the wireline tool 402. In another embodiment, the surface equipment may be located within an off-shore platform or cabin.

Figure 5:
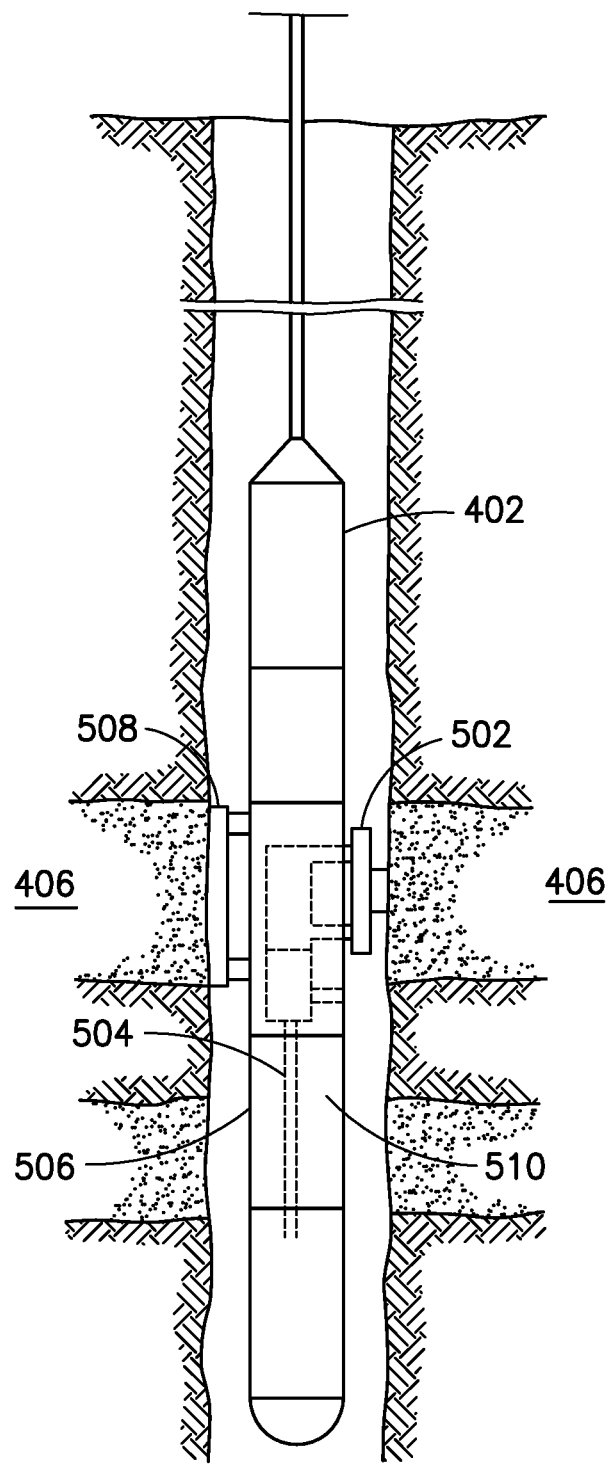
FIG. 5 is a schematic of a wireline tool in accordance with one embodiment.

As shown in FIG. 5, the wireline tool 402 includes an apparatus for acquiring fluid from a formation 406 and moving it into the wireline tool 402. The fluid flows from the reservoir 406, through the acquisition assembly (e.g. the probe) 502 and into a designated flow line 504 located within the housing 506 of the wireline tool 402. This fluid flow can occur naturally or be aided using a pump located in the wireline tool 402. While acquiring fluid from the formation 406, the wireline tool 402 may also be pressed against the formation 406 by a selectively extendable anchor 508 located on the wireline tool 402. Fluid in the wireline tool flow line 504 is analyzed by at least one fluid analysis system 510 installed in the wireline tool, including but not limited to a system to determine the asphaltene onset pressure of the fluid sample.

Figure 6:
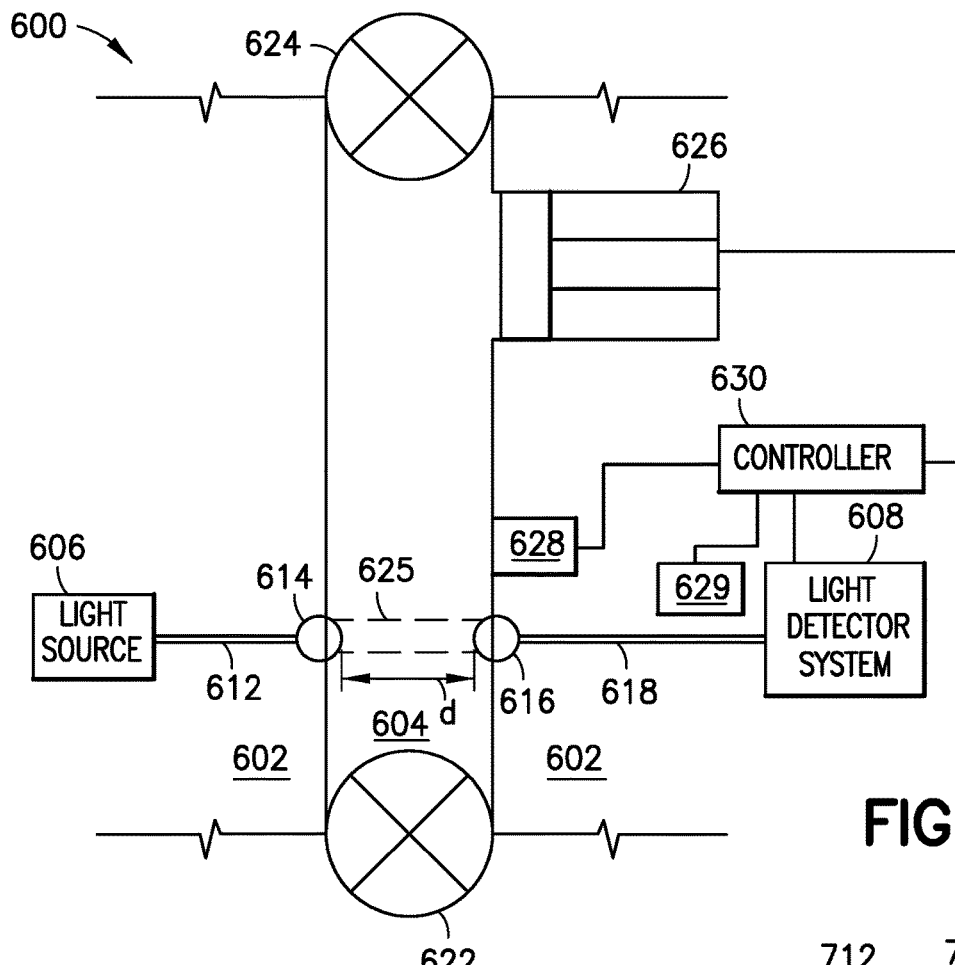
FIG. 6 is a schematic of a system which can be used to determine the asphaltene onset pressure of a formation fluid.

FIG. 6 is a schematic of a system 600 that can be used for measuring the asphaltene onset pressure of a fluid. The fluid sample is at least partly constrained in a detection chamber 604, which can be defined by or enclosed by a housing 602. This housing 602 can be made from various materials, such as steel or aluminum. In some embodiments, the fluid sample in the detection chamber 604 is obtained from the flowline 504 of the wireline tool 402. In some embodiments, channels comprising the detection chamber may have different diameters, including diameters less than 1 mm.

The asphaltene detection system shown in FIG. 6 also includes an optical source 606 and detection system 608. The optical source 606 can generate single or multiple wavelengths of light, and can produce wavelengths in the ultraviolet, visible and/or infrared part of the optical spectrum. This optical source can be coherent or incoherent: in the specific embodiment shown in FIG. 6, a tungsten halogen lamp is used as a light source. In other embodiments, this light source could be comprised of one or more of the following: tungsten halogen lamps, light emitting diodes (LEDs) or lasers. Light emitted by the light source 606 is collected into an optical fiber 612, which carries the light to an optical lens 614. This lens 614 collimates the light emitted from the fiber 612, directing it onto the fluid in the detection chamber 604. This lens 614 also serves as a pressure barrier, preventing the high-pressure sample from escaping the detection chamber 604. A second lens 616, which also acts as a pressure barrier, collects the light transmitted across the sample and directs it onto a second fiber 618. The second optical fiber 618 carries the transmitted light to the optical detection system 608. This optical detection system 608 includes one or more photodiodes.

In various embodiments, light from the source 606 interacts with the fluid sample in the fluid detection chamber 604 along a path 625 between two optical elements. These optical elements can be elements such as windows or lenses and may or may not also serve as a pressure barrier for keeping the sample contained in the fluid detection chamber. As shown in FIG. 6, the optical elements are ball lenses 614 and 616. The path 625 between them is of length d, and is a distance less than 2 mm. In other embodiments, this path length can be of different length, including lengths less than 1 mm. In other embodiments, a flat planar window may serve as a pressure barrier, and additional optical elements may be located outside of the fluid detection chamber 604.

Figure 7:
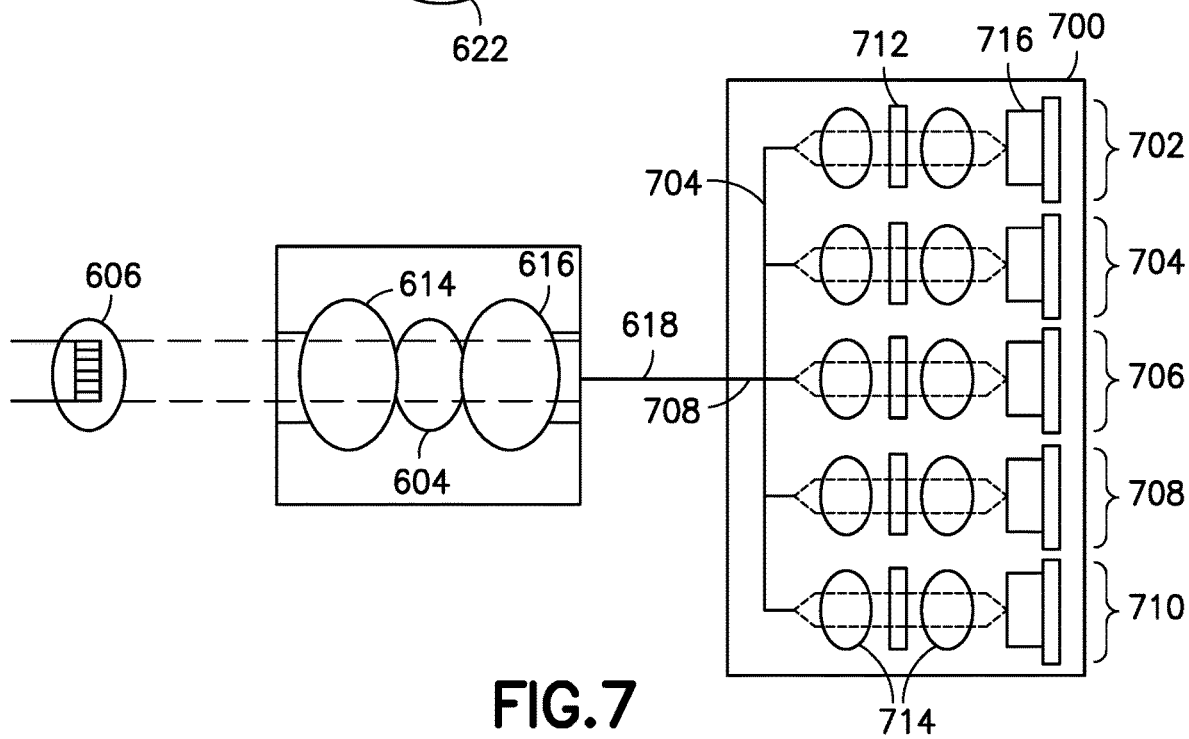
FIG. 7 is a schematic of a system for generating and detecting light in accordance with one embodiment.

In accordance with one embodiment of the present disclosure, a schematic of a light detector system 700 is seen in FIG. 7. This detector system 700 detects light generated by a light source 606. Light from the light source 606 is collimated in the fluid sample by a ball lens 614. A second ball lens 616 collects the transmitted light from the detection chamber 614. The second ball lens 616 directs light onto an optical fiber 618, which leads to an optical splitter 702. This splitter 702 splits the light into multiple unique detector modules 702, 704, 706, 708 and 710. In some embodiments, a detector module may include additional optics 714 and a detector 716. In other embodiments, the detector module may have additional optics 714, a detector 716 and an optical filter 712. The additional optics 714 can serve to focus light from the splitter 702 onto the detector 716. The optical filters 712 allow some wavelengths to pass, while blocking others, thereby allowing the detectors 716 to detect light at specific wavelengths. Without the filters 712, the detector 716 is a broadband detector, responding to a wide range of optical wavelengths. The detectors 716 (e.g. photodiodes) are sensitive to the intensity of the illumination transmitted through the filters 712 and focusing optics 714. In the example shown in FIG. 7, there are four filtered, wavelength specific channels 702, 704, 706, and 708 and one unfiltered, broadband channel 710.

The configuration and number of detector modules used in the detection system 700 can vary. The filters 712 can be selected and changed to allow measurement of various optical spectrum features. For example, the detector module 702 can be set to detect a wavelength in the hydrocarbon color range, such as 1070 nm. Module 704 can be set to detect water at 1445 nm, while module 706 can be set to 1600 nm to detect the hydrocarbon baseline. Module 708 can be used to detect the hydrocarbon absorption peak at 1725 nm. Module 710, without a filter, detects changes at all wavelengths to which the detector is sensitive. More or less than 5 detector modules or as few as one detector module can be used.

In FIG. 6, sample in the fluid detection chamber 614 can be isolated by the closing of two valves 622 and 624. These valves 622 and 624 can use a metal seal, such as is found in needle valves. In other embodiments, other types of values with different sealing mechanisms, such as rubber seals, can be used. These valves 622 and 624 can be opened to allow fluidic communication and exchange between the fluid in the detection chamber 604 and fluid in other parts of the wireline tool 402. Communication and fluid exchange can occur with fluid in (i) a sample bottle in the wireline tool, (ii) a flowline in the wireline tool, (iii) a sample waste disposal system in the wireline tool, or (iv) any combination of these elements. For example, with the valves 622 and 624 open, fluid from a flowline in the wireline tool 402 can flow through the fluid detection chamber and into a waste disposal system in the wireline tool 402.

With the valves 622 and 624 closed, the pressure of the sample isolated in the fluid detection chamber 614 can be changed by a pressure unit 626. This pressure unit 626 can take many forms. In one embodiment, it is a piston that can change the volume in the fluid detection chamber 614. By increasing the isolated sample volume, the piston decreases the sample pressure. Conversely, by decreasing the isolated volume, the piston increases the sample pressure. The pressure of the sample can be monitored by a pressure sensor 628. This pressure sensor 628 can be a strain gauge or a resonating pressure gauge.

In total, the minimum volume in the fluid detection chamber 604 can be less than 1 mL. Expansion of the isolated fluid detection chamber 604 volume to lower the sample pressure can increase this volume to be greater than 1 mL. In the case of limited volume of sample supply, the small volume of the fluid detection chamber allows for multiple sample volumes to be measured without risk of running out of the limited supply.

The temperature of the fluid sample in the fluid detection chamber 604 may be detected by the inclusion of a temperature detector 629 in the measurement system 600. This temperature detector 629 can be located in direct communication with the fluid sample. In a specific embodiment, the temperature sensor 629 is in thermal contact with the surface of the housing 602. The thermal conductivity of the housing allows the temperature detector 629 to measure the temperature of the sample fluid. One type of temperature sensor 629 suitable for measurement of the sample fluid is a resistive temperature detector (RTD).

The system 600 may also include a controller 630 to operate the different system components. The controller 630 may also aggregate and process signals generated by different components in the system. The controller 630 may communicate with the pressure unit 626 and pressure sensor 628 to control and monitor the pressure of the fluid sample. The controller 630 may sample this pressure at a rate between 10 and 60 Hz. The controller may also be in communication with the valves 622 and 624. The controller 630 may monitor the state of the valves 622 and 624 (e.g.—opened, closed, moving) and command the valves 622 and 624 to change state. The controller 630 may also communicate with the temperature detector 629 and monitor the temperature of the sample. The controller 630 may also be in communication with one or more of the detector modules in the light detector system 608. In one embodiment, the controller 630 may receive signals from the detector modules that are proportional to the intensity of light illuminating the detector modules. The controller 630 may monitor the signals from different detector modules at different rates, ranging between 1 and 120 Hz. In illustrative embodiments, the controller may monitor signals from the detector modules with wavelength filters, 702, 704, 706, and 708) at a rate of 1 Hz, while monitoring the signal from the detector module without a filter, 710, at a rate of 25 Hz.

Further details of devices and systems for determining bubble point pressure are provided in U.S. Pat. No. 8,910,514, Issued Dec. 16, 2014 and U.S. patent application Ser. No. 13/800,896, filed on Mar. 13, 2013 both of which are hereby incorporated by reference herein in their entireties.

Figure 8:
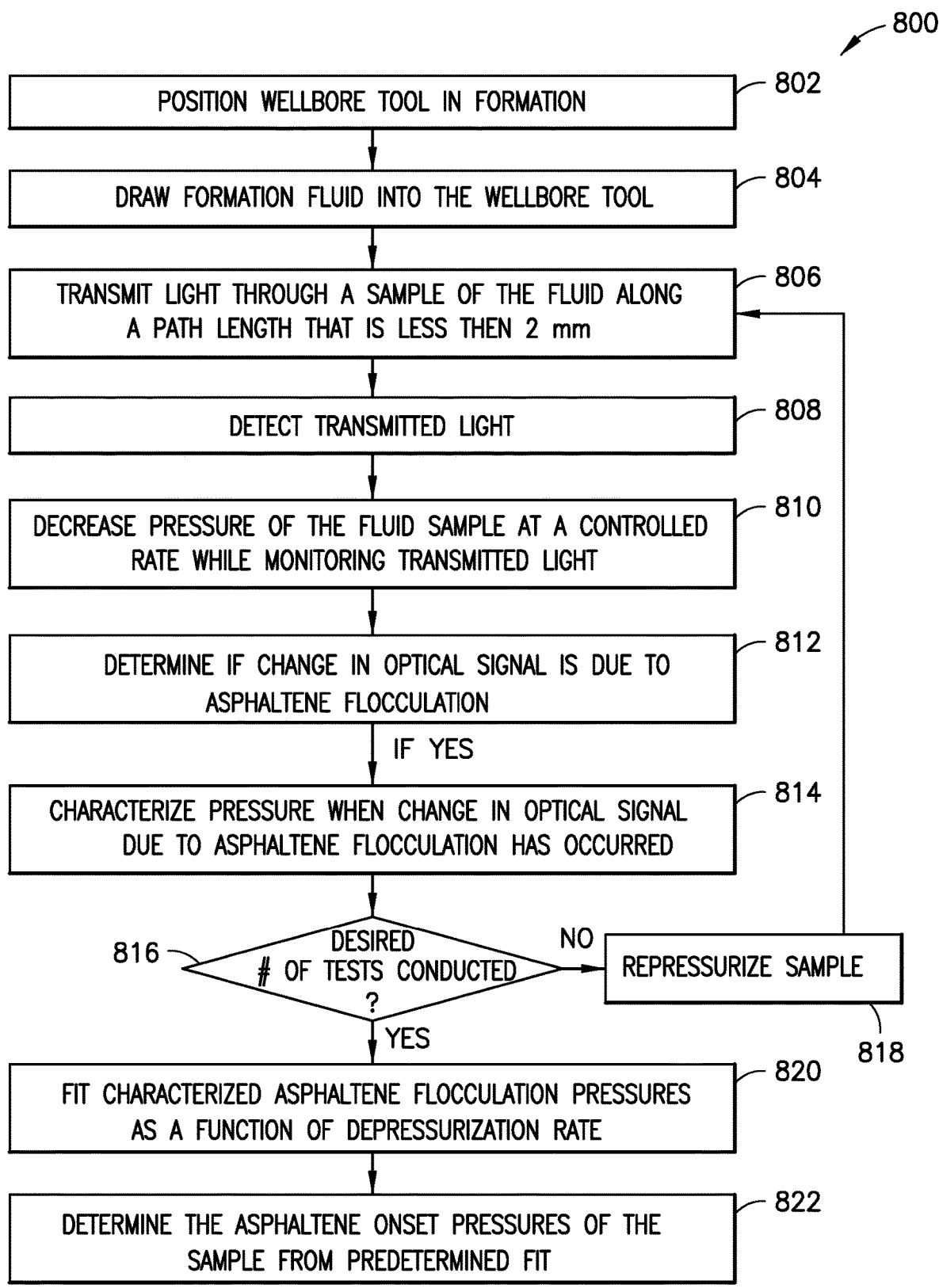
FIG. 8 is a flow diagram of a method for determining the asphaltene onset pressure of a fluid sample in accordance with one embodiment.

FIG. 8 shows a method 800 for determining asphaltene onset pressure of a fluidic sample. The method can be implemented by the system 600 and light detection system 700 previously described.

At 802, the wellbore tool 402 is positioned within a wellbore 404 that crosses (traverses) a reservoir formation of interest 406. The wellbore tool 402 may be a wireline tool or another wellbore tool, such as a logging-while-drilling (LWD) tool. FIG. 5 presents an example of such a tool.

At 804, formation fluid is brought into the wellbore tool 402. The formation fluid can be drawn into the wellbore tool by a probe 502 which protrudes into the formation. This probe, most commonly used when sampling from the formation, draws fluid from the formation. For other applications, such as production logging, a port on the side of the wellbore tool allows fluid in the wellbore to enter into the wellbore tool.

At 806, light is transmitted across a sample of formation fluid. At 808, the light transmitted by the sample is detected. The systems described in FIG. 6 and FIG. 7 enable these transmission and detection processes to be implemented. Sample fills a fluid detection chamber 604, which enables light to be transmitted through a region of the sample. In one embodiment, the path of the optical transmission is less than 2 mm. A light detector system 608, comprised of one or more detectors operating at one or wavelengths or range of wavelengths, detects the light transmitted through the sample.

At 810, the fluid sample pressure is decreased. This change is done in a controlled manner while light is being transmitted through the sample and detected by the light detection system 608. The pressure unit 626 can perform the pressure modification 810. During the process the pressure of the sample fluid is monitored by the pressure sensor 628. In one embodiment, the rate of pressure change of the sample is controlled. For example, the pressure of the fluid is decreased from 6000 psi to 1000 psi at a constant rate of −100 psi per second, taking a total of 50 seconds. In other embodiments, this constant depressurization rate can vary between −1 to −250 psi per second. Other pressure ranges and depressurization rates may be utilized. The change in pressure may be continuous or may be discretized into steps. In one embodiment, the rate of change of the volume of the fluid detection chamber 604 is controlled. For example, the volume of the fluid detection chamber 604 is increased from 1 mL to 2 mL at a constant rate of 10 µL per second, taking a total of 100 seconds. In other embodiments, this constant volumetric change can vary between −0.5 to 500 µL per second. This change in volume may be continuous or discretized. Other volumes and rates of change of volume may be used.

During pressure modification 810, the pressure of the fluid sample will decrease, eventually reaching the asphaltene onset pressure of the fluid. At and below the asphaltene onset pressure, the flocculated asphaltenes will scatter and absorb some of the light illuminating the sample, causing the intensity of the transmitted light to decrease. The amount of light scattered by the asphaltene flocs will depend on the wavelength of light as well as the number and size of the flocs. This differs from light scattered by bubbles formed at pressures at or below the bubble point pressure. Light scattered by bubbles will have no wavelength dependence.

At 812, an analysis may be performed to determine if a change in the optical signal was caused by asphaltene flocculation. This analysis distinguishes between a change in optical signal from the asphaltene flocculation and other phenomena, such as the formation of bubbles at pressures below the sample bubble point pressure. This analysis can be performed in many ways. In one illustrative embodiment, the wavelength dependence of the transmitted light is used to distinguish asphaltene onset from bubble formation. The intensity of the light transmitted through the fluid sample at one wavelength (e.g. 1070 nm) is compared to the intensity of the light transmitted through the fluid sample at a second wavelength (e.g. 1600 nm). This comparison can be done in many ways, such as subtracting the two signals or computing a ratio of the two signals. During a depressurization of the sample, a relatively larger change in the transmission of the shorter wavelength will indicate that asphaltene flocculation is occurring. Equal changes at the two wavelengths will indicate another cause for the decrease in optical signal, such as the presence of bubbles or debris. The two wavelengths should be chosen such that a relative change is obvious and unambiguously identifiable. Typically, a large relative change during asphaltene flocculation can be obtained by selecting two wavelengths that are distinct and are separate from each other. In one embodiment, the difference between the two wavelengths used is at least 100 nm. In another embodiment, the difference between the two wavelengths is at least 1000 nm. Other wavelength differences above or below 100 nm may be utilized.

To determine if asphaltene flocculation has occurred using wavelength dependent measurements, the light detection system 608 should detect the intensity of light transmitted across the fluid sample at two or more unique wavelengths. The controller 630 may both monitor or record the transmission detected at these wavelengths and by other optical modules and maintain the timing of these measurements as well. The controller 630 can be used to generate the wavelength dependent signal needed to determine if asphaltene onset has occurred. In one embodiment this wavelength dependent signal is a difference in the change in intensity of the two wavelength channels. The change in intensity of each wavelength channel from its starting value is determined. As shown in equation (1) the difference of the changes in intensity of the two wavelengths is then found according to $$\text{Wavelength Dependent Signal}(t) = [I(\lambda_1,t)I(\lambda_1,t_0)][I(\lambda_2,t)I(\lambda_2,t_0)] \quad (1)$$

where $I(\lambda_1, t)$ is the intensity of the light of one wavelength at time t and $I(\lambda_2, t)$ is the intensity of the light at time t at the second wavelength. $I(\lambda_1, t_0)$ is the intensity of the first wavelength at time $t_0$, which can be defined at any time in the measurement before the asphaltene onset has occurred. $I(\lambda_1, t_0)$ is a baseline measurement of the intensity of the first wavelength. Similarly, $I(\lambda_2, t_0)$ is a baseline measurement of the second wavelength.

The intensity I of the light as noted in equation (1) can be the signal measured in the detector modules located in the light detector system 608, or it can be a signal derived from the signals measured in the detector modules. In one embodiment, the derived signal is an optical density (OD), can be determined as:

$$\text{Optical Density} = \log_{10}\left(\frac{I_{out}}{I_{in}}\right) \quad (2)$$

where $I_{in}$ is the intensity of light illuminating the fluid sample $I_{out}$ is the intensity of light detected in a detector module after the light has passed through the sample. Optical density is representative of the absorption of the sample fluid, increasing in value as the transmission of light through the sample decreases.

Relationships other than the example in equation (1) can be used to determine the wavelength dependent signal. In one embodiment, the wavelength dependent signal is found by determining the ratio of the difference of the intensities of the two wavelengths at time t to the difference of intensities at time to. This relationship is defined according to:

$$\text{Wavelengt Dependent Signal}(t) = \frac{I(\lambda_1, t) - I(\lambda_2, t)}{I(\lambda_1, t_0) - I(\lambda_2, t_0)} \quad (3)$$

In another embodiment, the wavelength dependent signal is defined as the difference of the ratios of the intensity at two wavelengths at time t and time to. This relationship is defined by.

$$\text{Wavelengt Dependent Signal}(t) = \frac{I(\lambda_1, t)}{I(\lambda_2, t)} \frac{I(\lambda_1, t_0)}{I(\lambda_2, t_0)}$$

FIGS. 9A-9D present illustrative comparisons of measurements and wavelength dependent signals during a depressurization of fluids with and without an asphaltene onset pressure.

FIG. 9A shows two wavelength dependent signals determined using equation (1) during a depressurization of a fluid with bubble point but not asphaltene onset pressure. The wavelength dependent signals are shown as a function of pressure. Plot 902 was determined using wavelengths 1070 nm and 1600 nm. Plot 904 was determined using wavelengths 1445 nm and 1600 nm.

FIG. 9B shows the broadband signal 908 measured during the depressurization of a fluid with a bubble point but no asphaltene onset pressure. The broadband signal is shown as a function of pressure. The broadband signal was generated by a broadband (unfiltered) detector module described in FIG. 7.

FIG. 9C shows two wavelength dependent signals determined using Equation 1 during a depressurization of a fluid with both a bubble point and an asphaltene onset pressure. The wavelength dependent signals are shown as a function of pressure. Plot 902 was determined using wavelengths 1070 nm and 1600 nm. Plot 904 was determined using wavelengths 1445 nm and 1600 nm.

FIG. 9D shows the broadband signal (906) measured during the depressurization of a fluid with both a bubble point and an asphaltene onset pressure. The broadband signal is shown as a function of pressure. The broadband signal was generated by a broadband (unfiltered) detector module described in FIG. 7.

In FIG. 9A and FIG. 9C, a region of the wavelength dependent signals remain constant while the pressure of the fluid sample is decreased. In FIG. 9C, the wavelength dependent signals are constant until point 906, around 4000 psi. At pressures below 4000 psi, the wavelength dependents signals start to increase. The increase of plot 902 is greater than that of plot 904 because of the difference in wavelengths used to generate the two wavelength dependent signals. This increase is caused by the onset of asphaltene flocculation. A decrease in the broadband signal in FIG. 9D at the pressure can be seen at 906. This decrease is caused by the same asphaltene flocculation. In FIG. 9A, no increase in the wavelength dependent signals 902 and 904 can be seen, consistent with the sample fluid not having an asphaltene onset pressure.

In the broadband signals shown in both FIG. 9B and FIG. 9D, the bubble point pressure of the sample fluid is apparent at point 908. The decreases in optical signals at points 908 are due to the scattering of light by bubbles forming in the sample. In FIG. 9B the bubble point pressure is approximately 2070 psi. In FIG. 9A there is no corresponding increase or change in the wavelength dependent signals 902 or 904 at this or lower pressures (region 903). In FIG. 9D, the bubble point pressure is close to 2650 psi. At pressures at or below 2650 psi in FIG. 9C (region 905), the wavelength dependent signals stop increasing and level off.

Returning to FIG. 8, at 814, the optical signal is analyzed to find a pressure characterizing when the asphaltene flocculation started to alter the optical signal. This analysis is robust enough to not be sensitive to measurement noise, but still be sensitive to subtle changes due to asphaltene onset. This analysis can be done using any number of techniques. The pressure found at 814 is not necessarily the asphaltene onset pressure, but instead is a pressure that characterizes the pressure at which asphaltene flocculation started in a single measurement. The asphaltene flocculation pressure (AFP) depends on the kinetics of the depressurization and thus may be different then the asphaltene onset pressure found from an equilibrium measurement.

In one embodiment, a thresholding technique is used to analyze the optical signal to find a characteristic pressure of asphaltene flocculation. In this scheme, the change in optical signal is compared to a predefined value. In a scheme where the optical signal increases during asphaltene flocculation, the highest pressure at which the optical signal is larger than the predefined value is deemed the characteristic pressure of asphaltene flocculation. In a scheme where the optical signal decreases during asphaltene flocculation, the highest pressure at which the optical signal is smaller than the predefined value is deemed the characteristic pressure of asphaltene flocculation. This predefined value can be an absolute value or a percentage of the optical signal before asphaltene flocculation occurs.

In one embodiment, a technique to find the characteristic pressure of an optical signal involves fitting curves through two different regions of the optical signal, extrapolating those fits to other pressures and determining the pressure at which the two extrapolated curves intersect. For example, two regions that can be fit by different curves are the optical signal at pressures well above the asphaltene flocculation pressure and the optical signal at pressures immediately below the asphaltene flocculation pressure. The curves fitting these two regions can be extrapolated and will intersect at a pressure close to where the optical signal first begins to change due to the flocculation of asphaltenes. The curves fit to the measured data can be lines or more complex mathematical constructs. The fits can be done to regions of the optical signal that are, e.g., as small as 10 psi in pressure or larger than 1000 psi in pressure.

The optical signal used at 814 to find a pressure characterizing the flocculation of asphaltenes can be detected by any of the detector modules 702, 704, 706, 708, or 710 in the light detector system 608 shown in FIG. 7. The intensity can correspond to a broadband measurement of many wavelengths or the intensity from a detector monitoring a single wavelength. The optimal signal can also be derived from the signals generated by any of the detector modules. In one embodiment, the derived signal is the optical density of any of the intensities measured by the detector modules, where optical density is defined as in equation (2). In one embodiment, the derived signal is a normalized broadband optical transmission as shown in the following relationship:

$$\text{Normalized Broadband Optical Transmission} = 1 - 10^{-BBOD} \quad (5)$$

where BBOD is the optical density from the broadband scattering channel computed as defined in equation (2).

Figure 10:
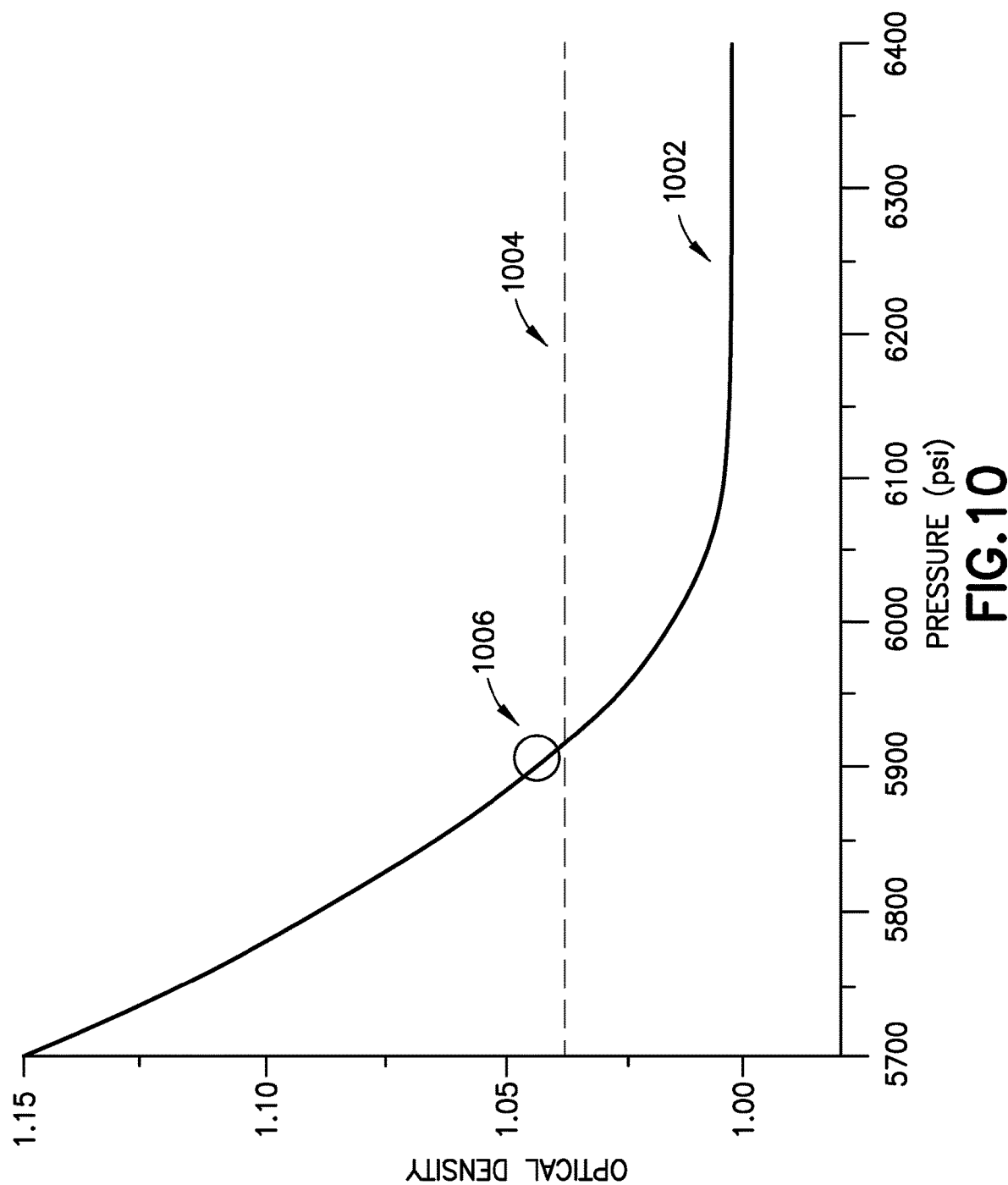
FIG. 10 is a plot showing one method for determining a pressure that characterizes the change in optical signal due to asphaltene flocculation.

FIG. 10 shows a plot demonstrating the use of a thresholding technique to determine a characteristic pressure at which asphaltene flocculation occurred during the depressurization of a fluid sample. The optical signal 1002 shown is the optical density derived from the broadband optical transmission measured in the detector module as defined in equation (2). As pressure of the fluid in the fluid detection chamber 604 is decreased at pressures above the asphaltene flocculation pressure, the density of the fluid decreases and less of the incident light is absorbed by the sample. The optical transmission increase and the optical density decreases. After asphaltene flocculation begins, the optical transmission decreases, and the optical density increases. The predefined threshold value of 1.035 is indicated by the dashed line 1004. The pressure of the point 1006 where the optical density rises above the threshold value 1004 is determined to be the pressure of asphaltene flocculation. In FIG. 10 this pressure is approximately 5900 psi.

Figure 11:
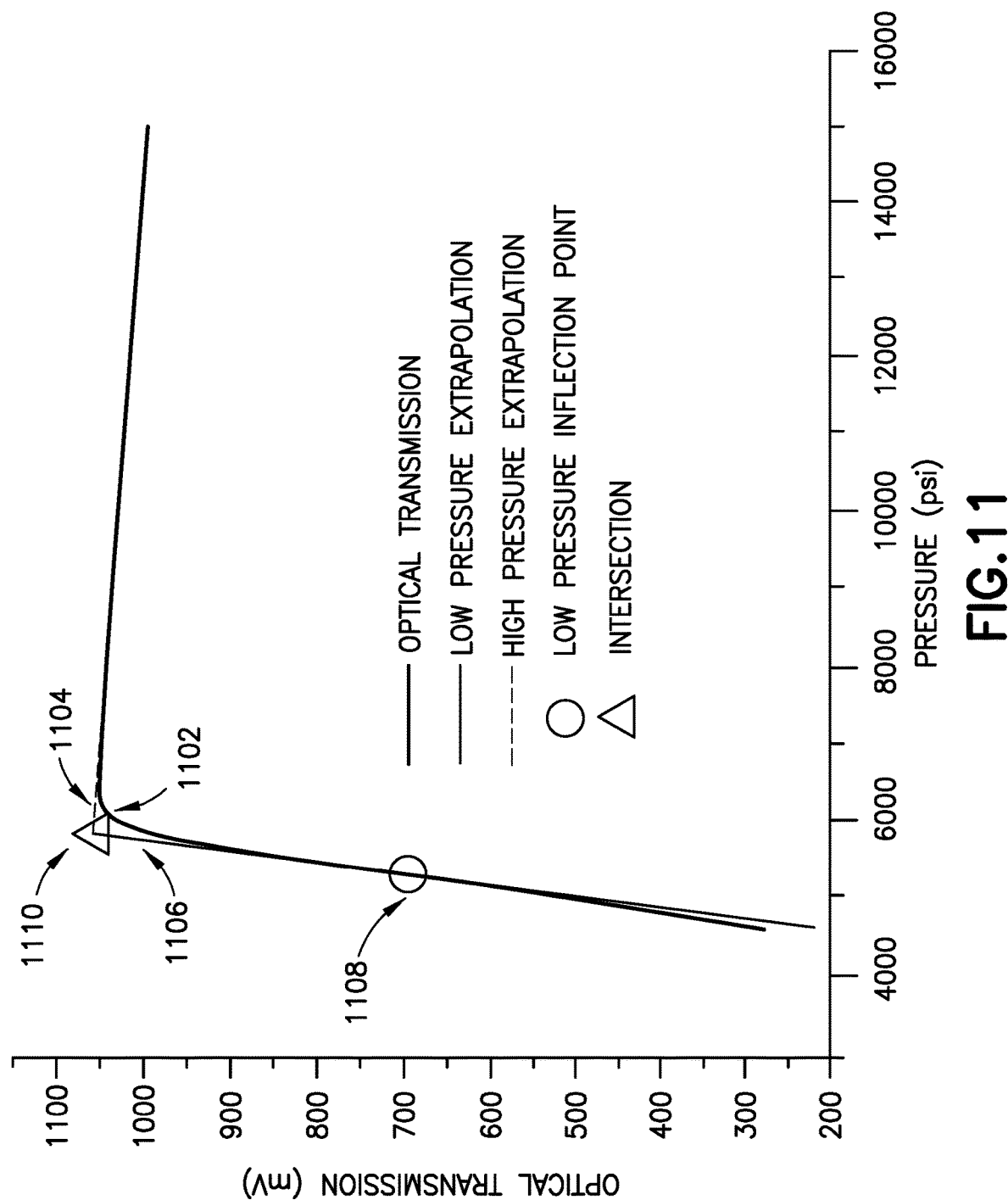
FIG. 11 is a plot showing another method for determining a pressure that characterizes the change in optical signal due to asphaltene flocculation.

FIG. 11 shows a plot demonstrating the use of a technique to fit curves through two different regions of the optical signal, extrapolating those fits to other pressures and then determining the pressure of asphaltene flocculation to be the pressure at which the two extrapolated curves intersect. The optical signal 1102 is the broadband optical transmission measured in the light detector module. One of the two curves 1104 fit to the optical signal 1102 is fit to the optical signal at pressures above the flocculation of asphaltenes. In FIG. 11 1104 is a line fit to the optical signal at pressures above 8000 psi. The second curve 1106 was fit at pressures below the pressure of asphaltene flocculation. In FIG. 11 this second fit 1106 was a line fit through the inflection point 1108 of the optical signal. The slope of the fit line 1106 is the slope of the optical signal at the inflection point with respect to the change in pressure. The characteristic pressure of asphaltene flocculation was determined to be the pressure (6000 psi) at which these two fits 1104 and 1106 intersect at 1110.

Returning again to FIG. 8, at 816, a determination is made as to whether a desired number of pressure flocculation determinations (e.g., at least two) have been conducted. If not, the method continues at 818 where the sample is repressurized in a controlled manner to permit another test of the sample. In one embodiment, the pressure of the fluid sample is returned to the same pressure or a pressure close to the pressure the sample was at when it was first introduced into the fluid detection chamber 604. In another embodiment, the fluid sample is pressurized to another pressure that is between the flocculation pressure previously detected and the pressure the sample was at when it was first introduced into the fluid detection chamber 604. In another embodiment, the fluid sample is pressurized to another pressure that is above the pressure flocculation pressure previously detected and may be below or above the pressure the sample was at when it was first introduced into the fluid detection chamber. Regardless, the repressurization 818 can be done with the pressure unit 626. During repressurization, the pressure of the sample fluid may be monitored by the pressure sensor 628. The repressurization 818 serves to help redissolve flocculated asphaltenes into the sample fluid. This redissolution aids in keeping the flocculated asphaltenes from settling on the optical elements 614 and 616 that allow light from the light source 606 to illuminate the sample and be collected into the light detector system 608.

After repressurization at 818, the method continues by repeating blocks 806, 808, 810, 812, and 814 so that a test including a minimum of two unique sequences of measurements is obtained. These two sequences should be performed with different depressurization rates in block 810. According to one embodiment, in order to facilitate the ultimate determination of the asphaltene onset pressure, the two depressurization rates may differ by at least 25 psi/sec. In one illustrative embodiment, one measurement sequence is performed with a depressurization rate of −100 psi/sec while one measurement sequence is performed with a depressurization rate of −10 psi/sec. In another illustrative embodiment, one measurement sequence is performed with a depressurization rate of −150 psi/sec while one measurement sequence is performed with a depressurization rate of −5 psi/sec. In other embodiments, method blocks 806, 808, 810, 812, and 814 and are conducted at least three times, each time at a unique depressurization rate. The results of two or more sequences of 806, 808, 810, 812, and 814, conducted at the same depressurization rate may also be combined to represent the measurement at a single depressurization rate. In one illustrative embodiment, two unique measurement sequences are performed at −100 psi/sec. The pressures found at 814 characterizing the asphaltene flocculation in each measurement are averaged to find an average pressure of asphaltene flocculation. This averaged pressure is used to represent the pressure of asphaltene flocculation for measurements at −100 psi/sec. For all measurements, fresh sample of a formation fluid (it being assumed that the samples are essentially uniform) may or may not be introduced into the fluid detection chamber 604 between each measurement.

Figure 12:
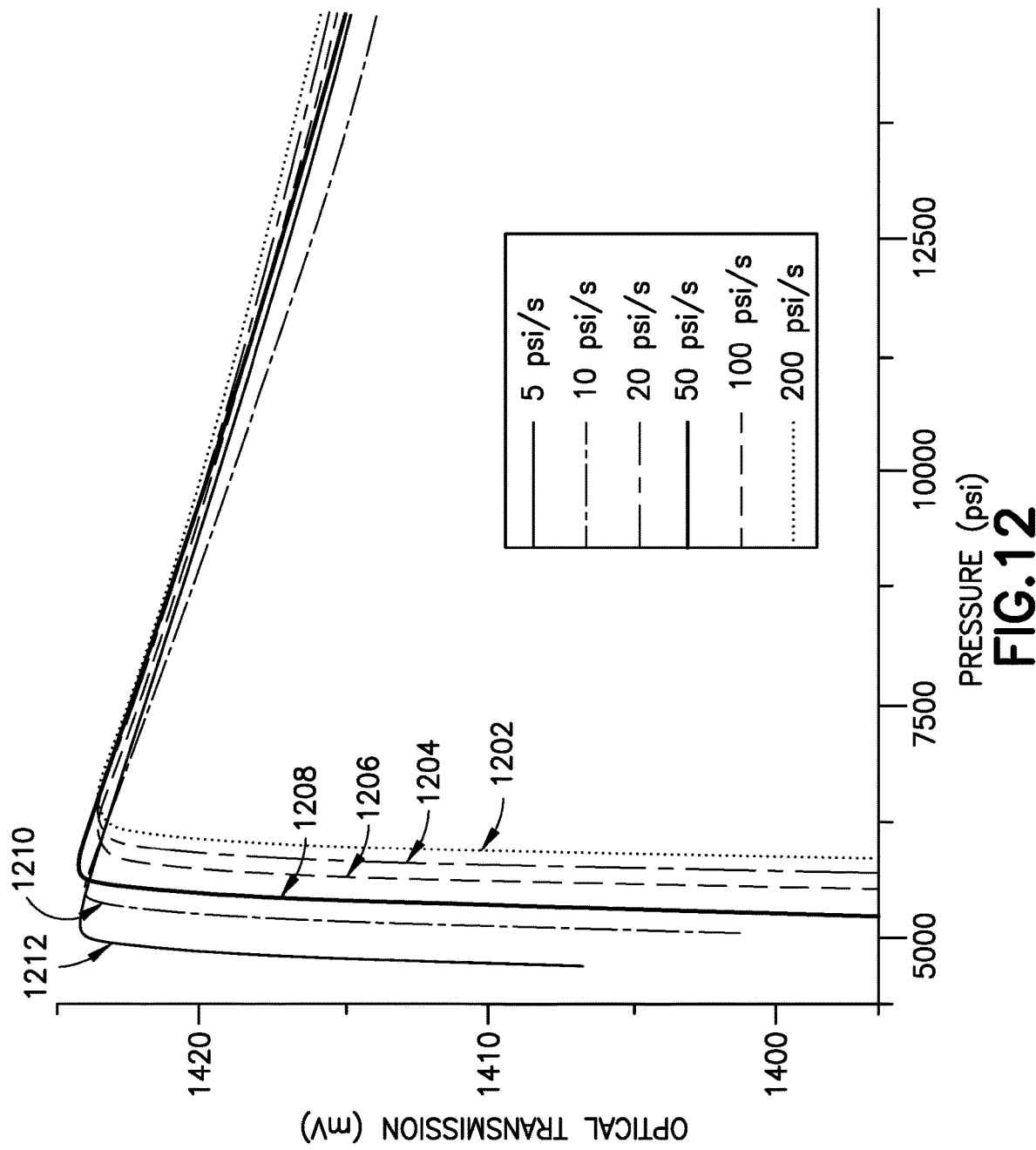
FIG. 12 is a plot of broadband optical transmission versus pressure for measurements at different depressurization rates.

FIG. 12 presents an example of broadband optical transmission data as a function of pressure measured during depressurizations of a sample at different depressurization rates. Accordingly, blocks 806, 808 and 810 of the method were applied to the sample six unique times. Each time, a different depressurization rate was used at 810. Measurements 1202, 1204, 1206, 1208, 1210 and 1212 were taken at depressurization rates of 5 psi/sec, 10 psi/sec, 20 psi/sec, 50 psi/sec, 100 psi/sec and 200 psi/sec, respectively. As can be seen in FIG. 12, in each measurement, there is a sudden decrease in optical transmission between 5000 and 6000 psi. This decrease is caused by the flocculation of asphaltenes in the sample. The pressure at which asphaltene flocculation occurs depends on the kinetics of the depressurization: faster depressurizations exhibit asphaltene flocculation at lower pressures then slower depressurizations.

Figure 13:
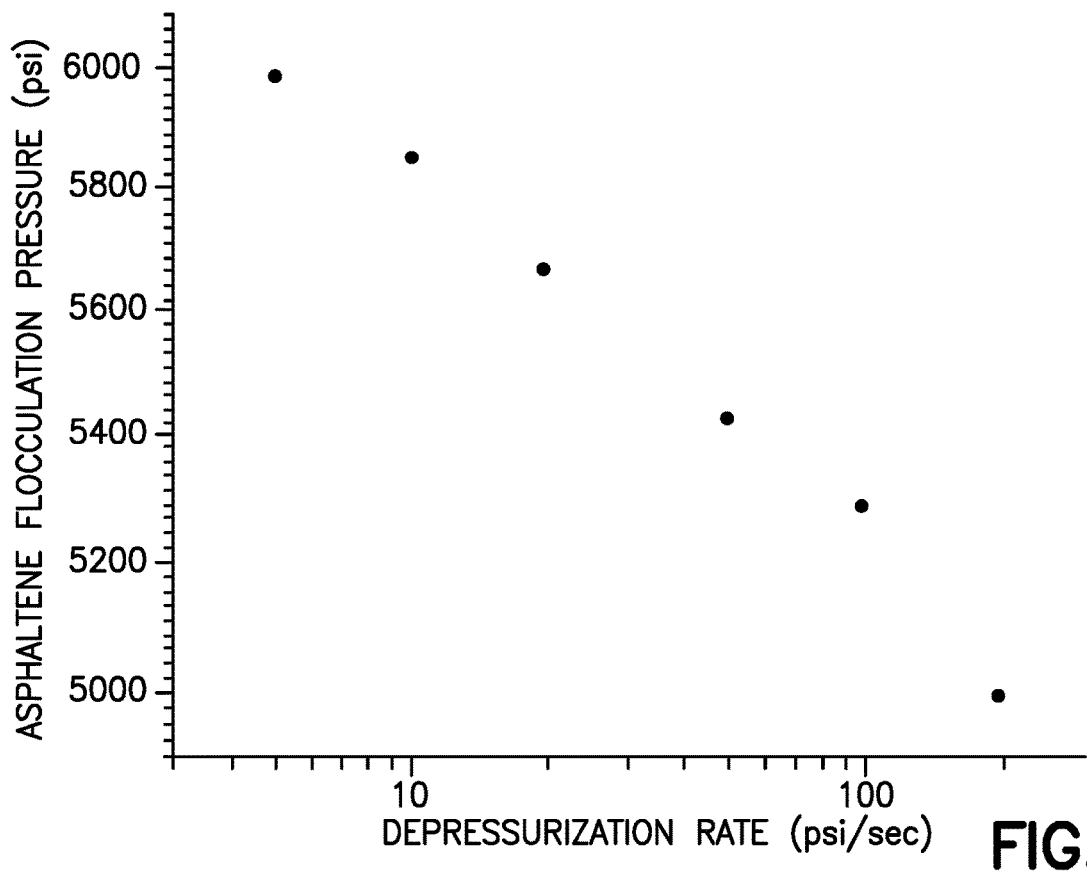
FIG. 13 is a plot of characteristic asphaltene flocculation pressure measured from an optical signal as a function of depressurization rate.

FIG. 13 presents the characteristic pressure of asphaltene flocculation found at 814 for the measurements shown in FIG. 12. The asphaltene flocculation pressure (AFP) is presented as a function of the depressurization rate. The relationship between the depressurization rate and the AFP is apparent. In this non-equilibrium measurement, at slower rates of depressurization the AFP is higher than for measurements at faster rates of depressurization. FIG. 13 presents six data points each at a different depressurization rate. Each of these data points represents the AFP of a unique depressurization. They were derived using an intersection of lines approach on the normalized broadband optical transmission (equation 5) of data in FIG. 11. In other embodiments, each data point could be the average of the AFP derived from two or more depressurizations performed at the same depressurization rate. For some sets of measurements, there may be more than six data points or as few as two data points.

Returning once more to FIG. 8, at 820 a fit to the characteristic pressures of asphaltene flocculation as a function of depressurization rate is made. In one embodiment, this fit can be made directly to the measured characteristic pressure of asphaltene flocculation. In another embodiment, the fit can be made to the difference between the non-equilibrium AFP determined at 814 and the actual asphaltene onset pressure (AOP) of the fluid, where the AOP determined from conventional laboratory measurements is assumed to be the true AOP of a fluid. The laboratory measurement is an equilibrium measurement: it is similar to a depressurization at a rate of 0 psi/sec and is not a function of the kinetics of depressurization.

Figure 14:
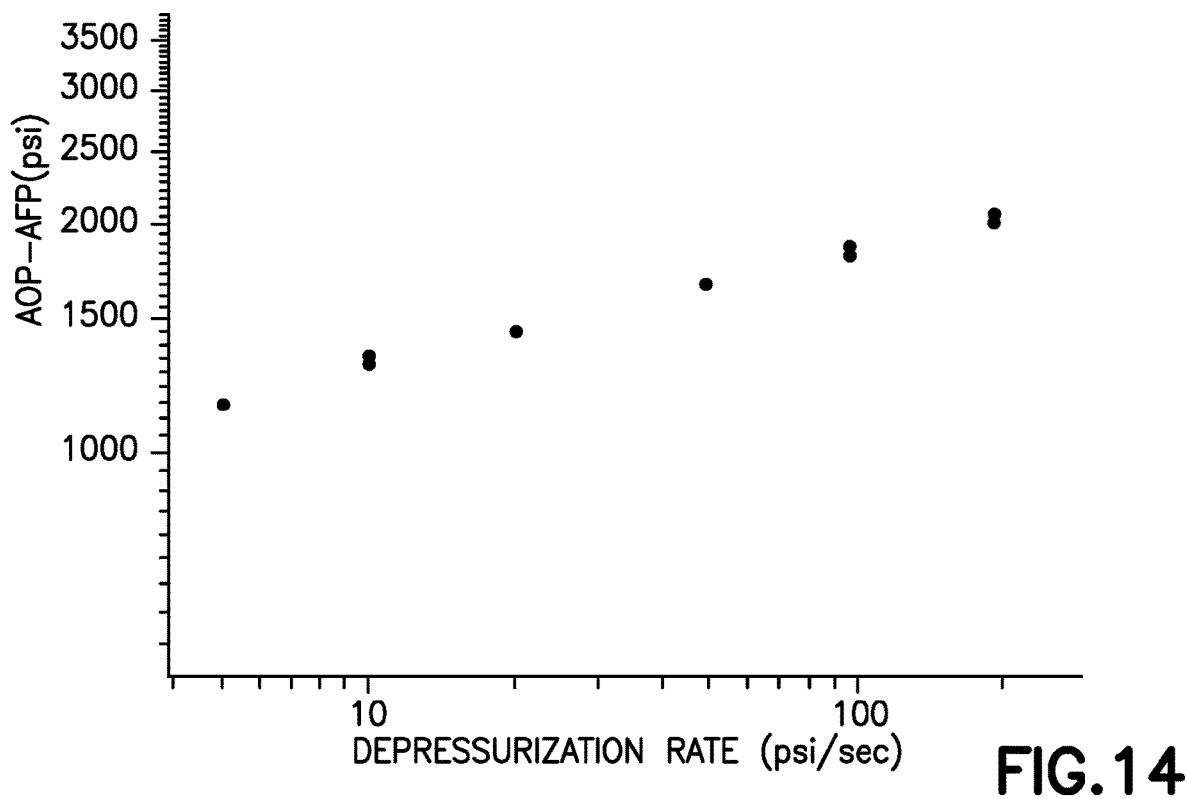
FIG. 14 is a plot of the difference between the standard laboratory based measurement of asphaltene onset pressure and the characteristic asphaltene pressure measured from an optical signal during a non-equilibrium depressurization as a function of depressurization rate.

The equation to which the fit is made can take many forms. In one embodiment the difference between the AFP and the AOP can be modeled as a power law, $$\text{AFP AOP} = Aq^B \quad (6)$$

where q is the depressurization rate, and A and B are the power law prefactor and exponent, respectively. FIG. 14 shows AOP-AFP plotted against the depressurization rate q.

In any fit performed at 820, one or more of the variables in the fitting equation can be set to a constant. Any constant chosen should result in minimal error for a wide range of samples. It might be possible to choose the constant based on other properties of the fluid, well, or field.

By way of example only, the power law exponent B in equation 6 can be set to a constant. As an example, the power law exponent may be set to a value of 0.15.

$$\text{AFP AOP} = Aq^{0.15} \quad (7)$$

Fits other than the power law shown above can be used at 820.

At 822, the asphaltene onset pressure of the fluid sample is found from the fit determined at 820. The fit determined at 820 is extrapolated to rates of depressurization not explicitly measured and which would be too time-consuming to be practical. In one illustrative embodiment, the fit can be extrapolated to a depressurization rate of 0 psi/sec. For power law fits of AFP-AOP, as given in Equations 6 and 7 and shown in FIG. 14, the extrapolation to a depressurization rate of 0 psi/sec allows an extrapolation to determine the AFP at 0 psi/second. This value is then taken to be the experimentally measured value of AOP and can be determined without knowledge of the laboratory measurement of AOP.

Figure 15:
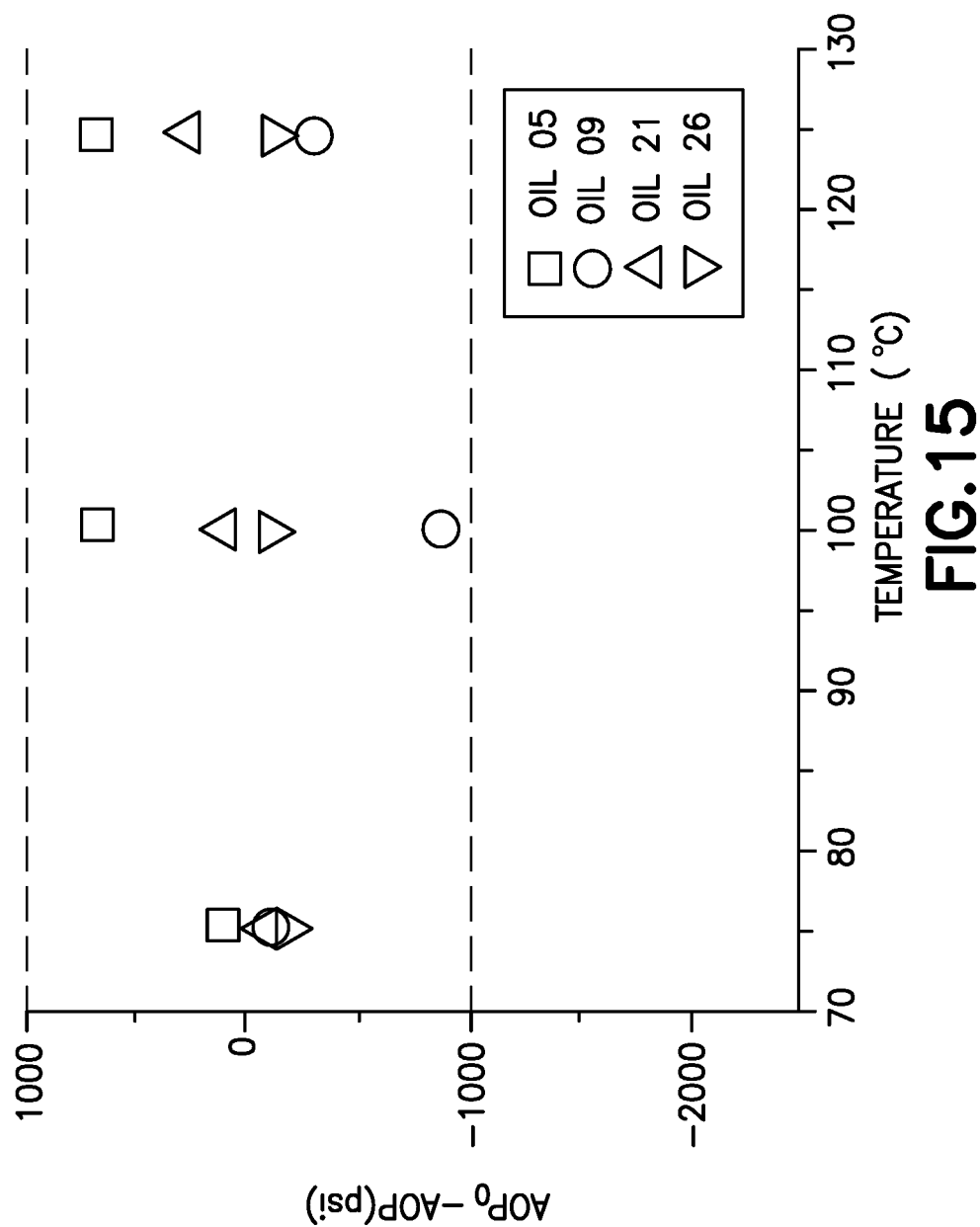
FIG. 15 is a plot of the difference between the asphaltene flocculation pressure (AFP) found from extrapolating a power law fit to a depressurization rate of 0 psi/sec and the laboratory determined value of AOP as a function of temperature for four different oil samples with a characterized AOP.

FIG. 15 presents the difference in asphaltene onset pressure determined according to the methods described herein (e.g., using the extrapolation technique of equation 7) ($\text{AOP}_0$) and the AOP of four oil samples (Oils 05, 09, 21 and 26) measured in a conventional laboratory setup (AOP). Each oil sample was characterized at three different temperatures, 75° C., 100° C., and 125° C. As is seen from FIG. 15, the results of the comparisons for all oil samples at 75° C. are excellent. In addition, the results of the comparisons for two of the oil samples (Oils 21 and 26) are excellent at all measured temperatures with a difference between laboratory AOP and calculated $\text{AOP}_0$ being less than approximately ±250 psi. The result of the comparisons for oil sample 05 at all temperatures was very good with a difference between laboratory AOP and calculated $\text{AOP}_0$ being less than approximately 700 psi; while the result for oil sample 09 at all temperatures was good, but not as good as the others, with a difference between laboratory AOP and calculated $\text{AOP}_0$ being less than approximately 1000 psi. It is noted that the differences between the determinations of the present method and those obtained in the laboratory are not necessarily due to inaccuracies in the results of the present method as the laboratory AOP measurements are not necessarily accurate to more than 500 psi. It is also noted that even if the results of the methods described herein are only accurate to ±1000 psi, such information is still valuable to an oil-field producer.

Some of the processes or methods described herein can be performed by a controller and/or processor, such as: (i) determining the asphaltene onset pressure of a fluid sample, (ii) receiving a transmitted light signal representative of an intensity of transmitted light at one or more wavelengths, (iii) determining a wavelength dependent signal, (iv) identifying a change within a broadband or wavelength dependent signal, (v) determining if an identified change in a detected signal is due to asphaltene flocculation, (vi) finding a pressure characterizing when the change in optical signal from asphaltene flocculation has occurred, (vii) fitting two or more characteristic pressures as a function of depressurization rate to a mathematical function, (viii) interpolating the fitted function to depressurization rates not measured, (ix) interpreting an output pressure signal from a pressure sensor, (x) controlling a pressure unit, (xii) opening and closing valves and (xiii) maintaining timing between transmitted light signals and an output pressure signal.

In one specific embodiment, both the controller and/or processor and the system for determining the asphaltene onset pressure are located within the wellbore tool. In this embodiment, all processes or methods performed by the controller can be performed in the wellbore tool. In another embodiment, the system for determining the asphaltene onset pressure is located within the wellbore tool, but the controller and/or processor is located at the surface. This location could be in a surface vehicle, such as the truck 412 in FIG. 4, or other surface equipment. In this embodiment the surface equipment performs some or all of the previously identified methods or processes (i)-(xiii). In another embodiment, there is more than one controller and/or processor, and the methods or processes are shared between the controllers. In yet another embodiment, the processes or methods are performed remotely at a location removed from the borehole tool and surface equipment.

As used, the terms 'controller' and 'processor' should not understood to be a particular type of device or system. The controller or processor may be a general-purpose computer, or a system built specifically for the wellbore tool. The controller may include a computer system. The controller or processor may also include a microprocessor, a microcontroller, or a digital signal processor for executing any of the methods and processes described above.

The controller or processor may also include individual, distinct electronic components coupled to logic devices. The electronic components and logic devices, such as integrated circuity or programmable logic devices, can be used to implement processes and methods outlined above.

The computer system may contain memory to store data transmitted from the system in the wellbore tool as well as the results of computations performed by the control system. The computer system may include a semiconductor memory device (e.g. RAM, ROM, PROM, EEPROM or Flash-Programmable RAM), a magnetic memory device, an optical memory device (e.g. a CD-Rom), a PC card or other memory device.

Computer program logic to be used on the computer processer can be used to implement process including (i)-(xiii) and other methods listed above. This computer program logic may be a source code, such as an object code, an assembly language, or a high-level language (e.g. C, C++ or JAVA). The computer program logic may also be a computer executable form. Non-transitory computer readable medium can be used to store the computer instructions. The computer processor can be used to execute the computer instructions. The instructions may be preloaded with a computer system or distributed on a communication system (e.g. the Internet or World Wide Web) via a server or website. The instructions also may be loaded onto the computer system from a portable, removable storage medium, such a CD-Rom or external hard drive.

Wireline logging operations, such as those illustrated in FIG. 4 and FIG. 5, are not the only situations where the embodiments of the present disclosure can be used. The embodiments of the present disclosure can be operated on other means of wireline conveyance, such as coiled tubing or drill pipe. The embodiments of the present disclosure can also be incorporated into other oil and gas related systems, such as those used in logging-while-drilling (LWD), sampling-while-drilling, measuring-while-drilling, or production logging.

The embodiments of the present disclosure can be used to analyze all types of hydrocarbons (e.g. dark oils, volatile oils, black oils and heavy oils). They are not restricted to a subset of hydrocarbon samples.

According to one aspect, the methods described herein are valuable in that they may be used downhole to obtain an estimate of the asphaltene onset pressure of a formation sample within a matter of minutes.

According to another aspect, the "answer product" of the AOP of the formation sample is considered a very important piece of information to the owner or producer of the hydrocarbon reservoir, as it can inform various determinations in the production of the hydrocarbons, including production pressures and rates.

The embodiments of the present disclosure are not restricted to oil and gas field applications. The embodiments can be used in a laboratory setting for oil and gas sample analysis. The embodiments can also be used in applications outside of the oil and gas industry, such as petrochemical refining and chemical manufacturing.

Although a few embodiments have been described in detail above, those skilled in the art will readily appreciate that many modifications are possible in the example embodiments without materially departing from the invention. Accordingly, such modifications are intended to be included in the scope of this disclosure as defined in the following claims.

What is claimed is:

1. A method for determining asphaltene onset pressure of a formation fluid, the method comprising:
   a. transmitting light through a sample of the formation fluid;
   b. detecting an intensity of the light transmitted through the sample of the formation fluid;
   c. decreasing a pressure of the sample of the formation fluid at a first controlled depressurization rate while monitoring the detected intensity of the light transmitted through the sample of the formation fluid;
   d. using results from (c), determining a first pressure at which the detected intensity of the light transmitted through the sample of the formation fluid changes due to asphaltene flocculation;
   e. repressurizing the sample of the formation fluid to, or introducing a second sample of the formation fluid at a pressure above the first pressure determined at (d);
   f. repeating (a) to (d) at least once using at least a second, different depressurization rate to determine a second pressure at which the detected intensity of the light transmitted through the sample of the formation fluid changes due to asphaltene flocculation;
   g. fitting at least the determined first and second pressures as a function of the first and second depressurization rates to a curve;
   h. determining the asphaltene onset pressure of the sample of the formation fluid from said curve.

2. The method of claim 1, further comprising:
   positioning a wellbore tool within a wellbore;

drawing the formation fluid into the wellbore tool; and performing (a) to (f) within the wellbore.

3. The method of claim 2, wherein said repressurizing the sample of the formation fluid or introducing the second sample of the formation fluid comprises introducing the second sample of the formation fluid.

4. The method of claim 1, wherein the sample of the formation fluid comprises a volume equal to or less than 1 mL.

5. The method of claim 1, wherein the transmitted light travels along a path length through the fluid sample that is less than 2 mm.

6. The method of claim 1, further comprising:
determining whether a change in the intensity of the light detected at is a result of flocculation of asphaltenes in the sample, wherein said detecting the intensity of the light transmitted through the sample of the formation fluid comprises detecting the intensity of the light transmitted through the sample of the formation fluid at a first and a second wavelength.

7. The method of claim 6, wherein said determining whether the change in the intensity of the light detected at (c) is a result of flocculation of asphaltenes in the sample comprises:
determining a wavelength dependent signal using the change in the intensity of the light at the first wavelength and the change in the intensity of the light at the second wavelength.

8. The method of claim 1, wherein said determining the first pressure at which the detected intensity of the light transmitted through the sample of the formation fluid changes due to asphaltene flocculation comprises:
determining a pressure at which the detected intensity of the light transmitted through the sample of the formation fluid changes past a predetermined threshold value.

9. The method of claim 1, wherein said determining the first pressure at which the detected intensity of the light transmitted through the sample of the formation fluid changes due to asphaltene flocculation comprises:
plotting the detected intensity of the light transmitted through the sample of the formation fluid as a function of the pressure of the sample of the formation fluid;
fitting a first curve to the plotted detected intensity for a first range of the pressure of the sample of the formation fluid;
fitting a second curve to the plotted detected intensity for a second range of the pressure of the sample of the formation fluid;
extrapolating the first fitted curve and the second fitted curve; and
determining the pressure at which the extrapolated first fitted curve intercepts the extrapolated second fitted curve.

10. The method of claim 1, wherein said fitting at least the determined first and second pressures as a function of the first and second depressurization rates to a curve comprises:
fitting the determined first and second pressures as a function of the first and second depressurization rates to a power law or other mathematical function.

11. The method of claim 10, wherein said power law or other mathematical function includes at least one variable and said at least one variable is set to a constant value.

12. The method of claim 10, wherein said power law or other mathematical function includes more than one variable and said more than one variable are set to constant values.

13. The method of claim 1, wherein said fitting at least the determined first and second pressures as a function of the first and second depressurization rates to a curve comprises:
fitting the difference between the determined first and second pressures and the actual asphaltene onset pressure of the formation fluid determined from conventional laboratory measurements to a power law or other mathematical function.

14. The method of claim 13, wherein said power law or other mathematical function includes at least one variable and said at least one variable is set to a constant value.

15. The method of claim 13, wherein said power law or other mathematical function includes more than one variable and said more than one variable are set to constant values.

16. The method of claim 1, wherein said determining the asphaltene onset pressure of the sample of the formation fluid from said curve comprises:
extrapolating said curve to a depressurization rate not directly measured in the sample.

17. The method of claim 16, wherein said extrapolating comprises:
extrapolating to a depressurization rate of 0 psi/sec.

18. The method of claim 1, wherein:
said decreasing the pressure of the sample of the formation fluid at the first controlled depressurization rate comprises:
decreasing the pressure of the sample of the formation fluid from an initial pressure value; and
said repressurizing the sample of the formation fluid to the pressure above the first pressure comprises:
repressurizing to said initial pressure value.

19. A system for determining asphaltene onset pressure of a fluid sample, the system comprising:
a fluid chamber;
a light source that generates light that is transmitted through the fluid sample;
a detector that detects light transmitted through the fluid sample;
a pressure control unit configured to vary the fluid sample pressure at a plurality of controlled depressurization rates; and
a controller configured to:
determine, for each of said plurality of controlled depressurization rates, a pressure at which an intensity of the light transmitted through the fluid sample and detected by the detector changes due to asphaltene flocculation;
fit the determined pressure for each of said plurality of controlled depressurization rates as a function of depressurization rate to a curve; and
determine the asphaltene onset pressure of the fluid sample from the curve.

20. The system of claim 19, wherein the transmitted light travels along a path length through the fluid sample in the fluid chamber that is less than 2 mm.

21. The system of claim 19, wherein at least said fluid chamber, said light source, said detector and said pressure control unit are incorporated into a wellbore tool.

22. The system of claim 21, wherein the wellbore tool further comprises a probe for withdrawing the fluid sample from a formation and into the wellbore tool.

23. The system of claim 19, wherein said fluid chamber has a volume equal to or less than 1 mL.

* * * * *